(12) United States Patent
Klein

(10) Patent No.: US 6,991,598 B2
(45) Date of Patent: Jan. 31, 2006

(54) MINIATURE CLOTHING ATTACHABLE VIBRATOR

(76) Inventor: Eric A. Klein, 235 College Ave., Mountain View, CA (US) 94040

( * ) Notice: Subject to any disclaimer, the term of this patent is extended or adjusted under 35 U.S.C. 154(b) by 368 days.

(21) Appl. No.: 10/292,792

(22) Filed: Nov. 12, 2002

(65) Prior Publication Data

US 2003/0181784 A1   Sep. 25, 2003

Related U.S. Application Data

(60) Provisional application No. 60/367,107, filed on Mar. 25, 2002.

(51) Int. Cl.
*A61F 5/00* (2006.01)
(52) U.S. Cl. ...................................................... 600/38
(58) Field of Classification Search .................. 600/38; 601/46–80, 81, 98
See application file for complete search history.

(56) References Cited

U.S. PATENT DOCUMENTS

| | | | |
|---|---|---|---|
| 2,286,089 A | 6/1942 | Harris | |
| 2,350,817 A | 6/1944 | Purves et al. | |
| 2,918,055 A | 12/1959 | Boerger | |
| 3,623,481 A | 11/1971 | Curran | |
| 4,116,233 A | 9/1978 | Scaduto | |
| 5,499,429 A * | 3/1996 | Higginbotham | 24/3.11 |
| 5,519,292 A | 5/1996 | Taylor et al. | |
| 5,601,529 A | 2/1997 | Wollman | |
| 5,621,384 A * | 4/1997 | Crimmins et al. | 340/539.3 |
| 5,660,597 A | 8/1997 | Fox et al. | |
| 6,193,678 B1 | 2/2001 | Brannon | |
| 6,203,509 B1 | 3/2001 | Duboff | |
| 6,332,862 B1 | 12/2001 | Zandman | |
| 6,382,815 B1 | 5/2002 | Klearman et al. | |
| 6,419,649 B1 | 7/2002 | Klein | |
| 2002/0120991 A1 * | 9/2002 | Cacka et al. | 15/22.1 |

* cited by examiner

*Primary Examiner*—John P. Lacyk
(74) *Attorney, Agent, or Firm*—Thomas M. Freiburger

(57) ABSTRACT

A miniature sexual aid device comprising a battery powered electric vibrator which attaches to the user's clothing. The sexual aid device includes a vibration motor, a button cell battery, a moisture resistant housing that contains the motor and battery, and a clip for attaching the device to the clothing material. The retaining clip may use magnets, friction or pins to attach to clothing material. The device is no larger than some jewelry broaches or pins and may be shaped and colored to be worn as an ornament.

5 Claims, 3 Drawing Sheets

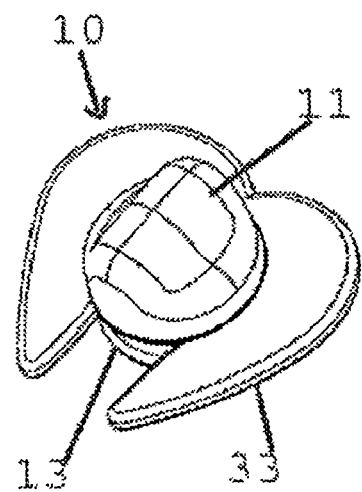
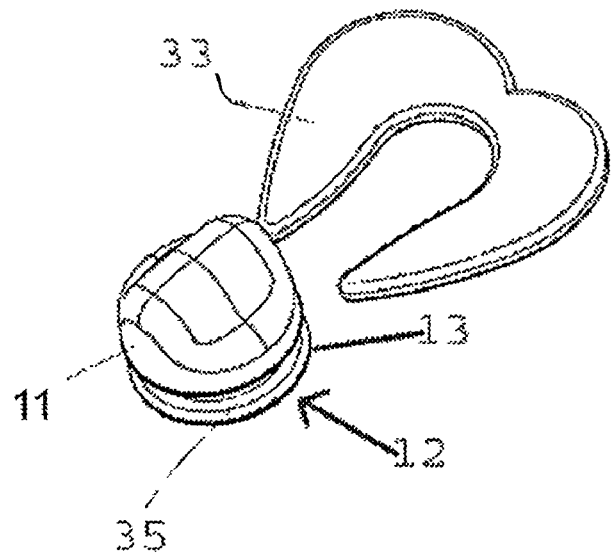
Fig. 5　　　　　　　　　Fig. 6
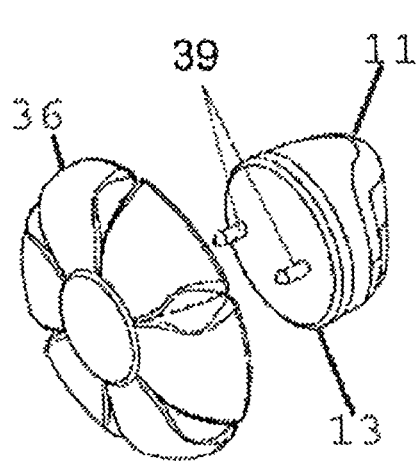
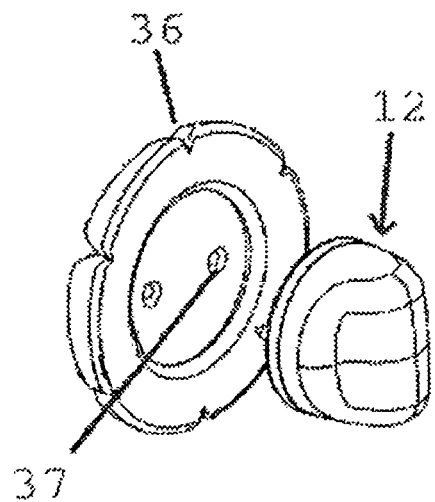
Fig. 7　　　　　　　　　Fig. 8

MINIATURE CLOTHING ATTACHABLE VIBRATOR

This application claims benefit of provisional application No. 60/367,107, filed Mar. 25, 2002.

BACKGROUND OF THE INVENTION

This invention relates to a vibrating sexual aid device, specifically to a miniature hands-free device that is worn on the body and that attaches to an article of clothing.

Battery powered vibrating devices are well known in the art. Hands-free genital vibrators are less common, but have been produced and offered for sale. Known devices are worn either internally or externally. Internally worn devices are outside the scope of this application and will not be discussed further.

The smallest of the known external hands-free devices are more than two inches in their largest dimension, weigh several ounces, and are powered by AA cell or larger batteries. The known devices are held in proximity to the genital area with a special harness. Although details differ, the harness looks generally like an athletic supporter and consists of a waistband or belt, a fabric pouch at the front, and two straps which attach to the pouch, pass through the legs, and attach at the rear of the waistband.

These known devices suffer from several disadvantages including their relatively large size, obtrusiveness, unattractive appearance, cost, and difficulty of use.

U.S. Pat. No. 6,193,678 describes a vibrator vest for massage.

SUMMARY OF THE INVENTION

A miniature sexual aid device of the invention comprises a battery powered electric vibrator which attaches to the user's clothing. The device in a preferred embodiment is approximately 1 inch in diameter and weighs approximately 1 ounce. The sexual aid device includes a vibration motor, a button cell battery, a moisture resistant housing that contains the motor and battery, and a clip for attaching the device to the clothing. The clip may be formed and colored to create decorative shapes and designs.

The two part housing preferably is roughly cylindrical in shape. Rotating the upper housing in relation to the lower housing operates an on-off switch and, if rotated further, twists open the housing to provide access to the battery. In a preferred embodiment the housing, exclusive of the retaining clip, is smaller than a cylinder 0.75 inch in diameter and 0.75 inch high and weighs less than 0.5 ounce. The housing is moisture resistant.

The retaining clip may be offered in a variety of styles. Each style allows the device to be easily and quickly attached and detached. The clip securely affixes the device to clothing without damaging the garment material.

Accordingly several objects and advantages of my invention are:
to provide a hands free vibrating sexual aid which attaches securely to clothing without damaging the garment;
to provide a clothing mounted vibrating sexual aid which may be shaped and colored in such a way as to be worn as an ornament;
to provide a miniature hands free vibrating sexual aid which, due to its tiny size, is amusing, unobtrusive and non-threatening; and
to provide a hands free vibrating sexual aid which vibrates strongly enough to be stimulating but not so strongly that it causes numbing.

Further objects and advantages of my invention will become apparent from a consideration of the drawings and the ensuing description.

DESCRIPTION OF THE DRAWINGS

FIGS. 5 and 6 are perspective views of a modified form of the invention, with a slide-on material clip as a different means of attachment.

FIGS. 7 and 8 are perspective views of another form of the invention, with a pin-and-socket material clip for attachment to clothing fabric.

DESCRIPTION OF PREFERRED EMBODIMENTS

Figure 1:
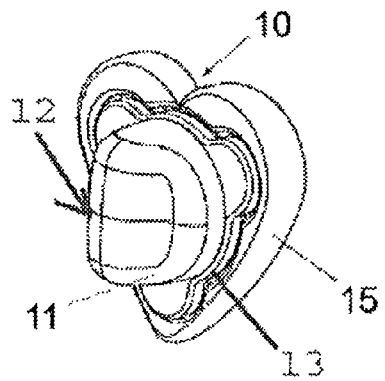
FIG. 1 shows a rear perspective view of one embodiment of the invention.

FIG. 1 shows in perspective one preferred embodiment for carrying out the principles of the invention. The vibrator device 10 has a vibration module 12 with an exterior moisture resistant housing which separates into an upper or motor housing 11 and a lower or battery housing 13. ("Upper" and "lower" are only used for convenience of description and not to imply particular orientation of the device 10 in use.) The upper housing and lower housing twist apart to enable battery replacement and snap together to reassemble the device. A heart shaped front plate 15 in this embodiment serves as a retaining clip and removably attaches to the vibration module 12. The housings can be referred to as first and second housing, or first and second housing components, or the assembled two housings can simply be referred to as a housing. Reference to two housings includes construction wherein one "housing" is simply closure plate.

Figure 2:
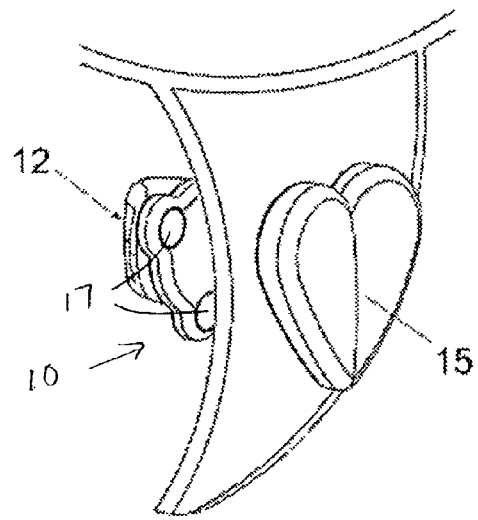
FIG. 2 shows a perspective view of the invention with a heart shaped front plate, showing how the device attaches to an article of clothing.

FIG. 2 is a perspective view of the preferred embodiment of the vibrator showing the positions of vibration module 12 on the inside of a pair of panties and the heart shaped front plate retaining clip 15 on the outside. This embodiment uses magnetic force to removably attach the front plate to the vibration module, sandwiching the garment material, and holding the device in place. Magnets are seen at 17.

Figure 3:
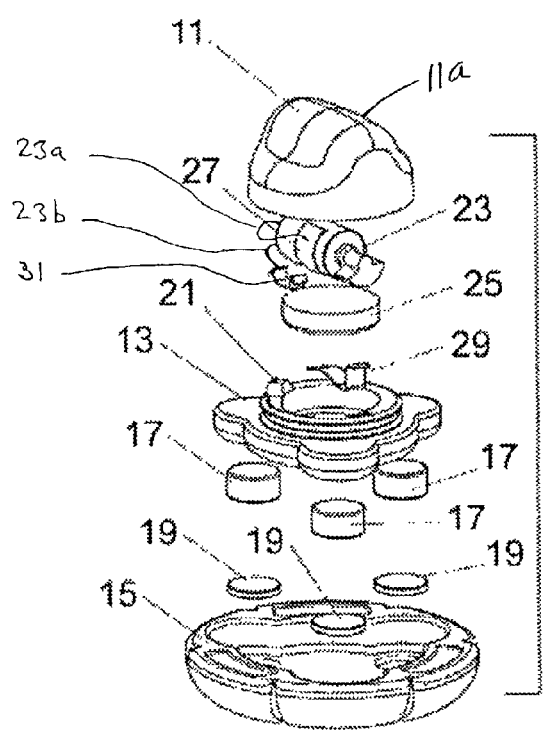
FIG. 3 shows a disassembled perspective view of the invention, in a slightly modified embodiment with a different front plate.

FIG. 3 is a disassembled or exploded perspective view of this preferred embodiment of the vibrator, in this case with a different decorative front plate 15a. The upper housing 11 contains a transversely mounted vibrator motor 23, a negative battery contact 27, and a switch contact 31. A negative motor wire 23a is connected to the negative battery contact 27 and a positive motor wire 23b is connected to the switch contact 31. The lower housing 13 contains a battery 25 and a positive battery contact 29. The positive battery contact 29 touches the battery and also extends upward from the lower housing 13 in such a way that it may touch the switch contact 31 when the unit is assembled. In the assembled configuration the motor 23 is engaged in a recess (not shown) of the upper housing, and the vibrator motor casing or the motor's battery contact 27 engages against the battery 25. In this preferred embodiment rotating the upper housing 11 in relation to the lower housing 13 powers the device on and off by moving the switch contact 31, which is secured to the upper housing 11, into contact with the battery contact 29.

In this embodiment, three magnets 17 are permanently fixed into sockets on the bottom of the lower housing 13. Three steel (or other ferrous metal) inserts 19 are permanently fixed into sockets in the front plate 15 in such a way that when the unit is assembled the magnets and steel inserts are in contact. The positions of the magnets and steel inserts can be reversed.

Note that the described configuration is preferred, in that the vibrator motor can reside in an elongated top area 11a of the upper housing, but the battery and vibrator motor positions can be reversed if desired. The housings are referred to as first and second housings in the claims, and no implication as to necessary position should be taken from reference herein to upper and lower positions for each housing. The top area 11a as shown in the drawing may be rounded and without sharp edges, as a sexual stimulation tip that can be worn and positioned as shown in FIG. 2.

The vibrator motor 23 may be of a known type used in silent pagers, usually known as a vibration motor or pager motor. For example, the motor can be one identified as "cylindrical DC motor of permanent magnet", Model OTL-6SL, manufactured by Jinlong Machinery & Electronic Co., Ltd. Of Yeuquing, Zhejiang, China. This particular cylindrical motor 23 is about 10 mm in length and about 6 mm in diameter. Preferably the vibrator motor is less than about 20 mm in length and less than about 10 mm in width or diameter to suit the objectives of the invention.

Figure 4:
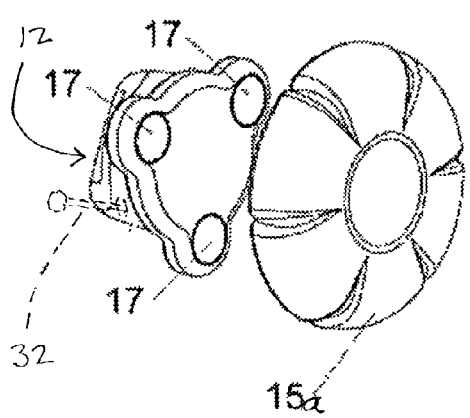
FIG. 4 shows a front perspective, partially disassembled view of the invention with a flower shaped front plate.

FIG. 4 shows a preferred embodiment 10 of the vibrator with magnets 17 visible on the underside of vibration module 12. As in FIG. 3, the front plate 15 is formed in the shape of a flower. Also, FIG. 4 shows in dashed lines an alternative form of on/off switch 32, a simple toggle, twist or slide switch (or other appropriate switch) mounted on the side of the housing. This is an alternative to the housing rotation switch described above.

FIGS. 5 and 6 show an alternate embodiment of the vibrator in which the device is held in place with a slide-on material retaining clip 33. The upper housing 11 snaps together with the lower housing 13 to form the vibration module 12. The U-shaped slide-on material clip 33 mates with a clip slide recess 35, or a pair of opposed recesses, that are integral with the lower housing 13 in this embodiment. Reference to "recesses" is intended to embrace either form. Otherwise the construction and function are similar to the embodiment shown in FIG. 3. When attached to a garment, the vibration module 12 is worn inside the garment and the slide-on clip 33 is worn on the outside.

FIGS. 7 and 8 show an alternate embodiment of the vibrator in which the device is held in place with a pair of pins (or at least one pin) 39 that mate with a pair of pin sockets 37 in a pin-and-socket front plate 36. The front plate 36 is flower shaped in this drawing as an example. When attached to a garment, the vibration module 12 is worn inside the garment and the front plate 36 is worn on the outside. The pins extend through the fabric and engage the sockets by friction. The number of pins and sockets can vary and their positions can be reversed from what is shown.

Figure 9:
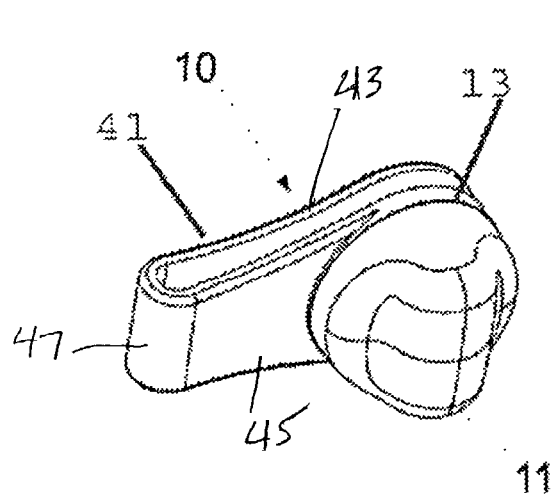
FIGS. 9, 10 and 11 are perspective views of a further form of the invention, with a side-mount material clip.
Figure 10:
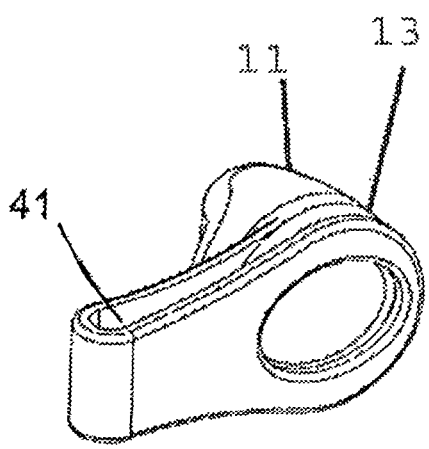
Figure 11:
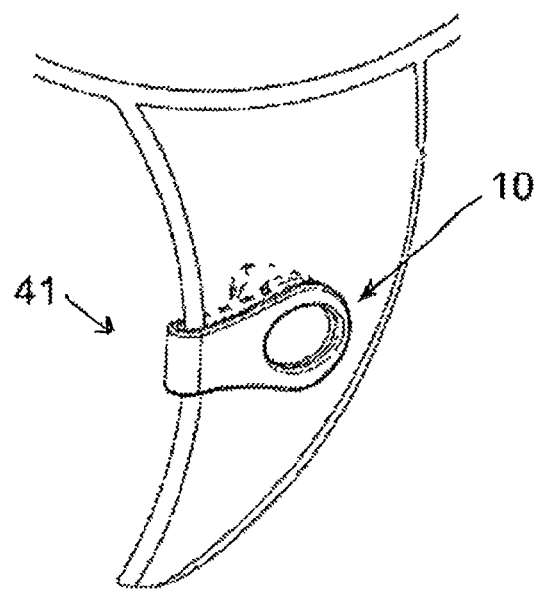

FIGS. 9–11 show an alternate embodiment of the vibrator in which the device is held in place with a side-mount material clip 41, somewhat like a money clip or tie clip, having two spring-loaded arms 43 and 45 connected at an outer end 47 and adapted to pinch the fabric between the arms when attached by lateral sliding to the article of clothing. This embodiment attaches to a garment using a structure similar to a paper clip or other pinch-type clip as noted above.

The terms "retaining clip", "retaining means", "clip", "clip means", etc. are to be understood as meaning those forms of clips shown (magnets, pins, slide engagements, pinch clips like a money clip, etc.), and all equivalent structures capable of engaging clothing so as to position the vibrator portion inside, and not to include bands or straps, such as a ring or watch.

In operation of any of the embodiments, the user inserts the vibration module into the body side of an article of clothing, most commonly a pair of panties, then affixes the front plate to the exterior of the material, sandwiching the material. For FIGS. 9–11 the entire device is slid in from ones side. The user powers the device on by twisting the upper housing, in one preferred embodiment. Testing has shown that a watch battery can power the device for a period of between 30 and 90 minutes depending on the storage capacity of the battery and the power consumption of the motor.

Accordingly, the miniature clothing attachable vibrator of this invention provides a small, lightweight vibrator that attaches securely yet comfortably to clothing. The vibrator is quick and easy to attach and detach, and may be worn comfortably and undetectably under outer garments and does not interfere with the user's normal activities. The vibrator's small size makes it unobtrusive and non-threatening. The outer cover may be produced in a number of attractive and amusing shapes such as flowers, hearts, stars, animal shapes, etc. The device contains few parts and may be inexpensively produced.

Although the description above contains many specifics, these should not be construed as limiting the scope of the invention but as merely providing illustrations of some of the presently preferred embodiments of this invention. Thus, the scope of the invention should be determined by the appended claims and their legal equivalents, rather than by the examples given.

I claim:

1. A sexual aid device, comprising:
   a first housing,
   a second housing, having a recess containing a battery,
   One of the housings having a rounded sexual stimulation tip without sharp corners positioned to provide sexual stimulation to a wearer when the sexual aid device is worn on an article of clothing,
   the first housing being connected to the second housing, with the battery and a vibrator motor contained by the two housings,
   electrical connections within the two housings and connected to the vibrator motor and the battery, including a switch enabling the device to be turned on or off, to activate or deactivate the vibrator motor, and
   a retaining clip for securing the device to an article of clothing, by engagement with the clothing and one of the housings, the retaining clip comprising a component to be worn on the exterior of the article of clothing, the component being separate from and detached from both housings and having means for engagement with said one of the housings such that the article of clothing is sandwiched between the clip device and the housing without contact between the component and the housing.

2. The device as described in claim 1 wherein said means for engagement comprises at least one magnet fixed to one of the retaining clip and said one housing, and at least one ferrous metal insert secured to the other of the clip and said housing, for attracting the housing to the retaining clip with the clothing between.

3. The device as described in claim 1, wherein the first housing includes a switch contact positioned such that rotation of the upper housing relative to the second housing in opposed rotational directions will switch the device on and off, serving as said switch.

4. The device as described in claim 1, wherein the means for engagement comprises a U-shaped outer component serving as said retaining clip, and peripheral recesses formed by one of said housings for sliding engagement with the U-shaped outer component, whereby clothing fabric can be pinched between the recesses and the U-shaped component upon such sliding assembly.

5. The device as described in claim 1, wherein the switch comprises a hand-operated toggle switch extending at the exterior of one of the first and second housings.

* * * * *